United States Patent
Hendrikx

(10) Patent No.: US 10,022,694 B2
(45) Date of Patent: Jul. 17, 2018

(54) CALIBRATION DEVICE FOR A THERMAL CYCLER

(71) Applicant: CYCLERTEST B.V., Landgraaf (NL)

(72) Inventor: Michael Thomas Hendrikx, Landgraaf (NL)

(73) Assignee: CYCLERTEST B.V., Landgraaf (NL)

( * ) Notice: Subject to any disclaimer, the term of this patent is extended or adjusted under 35 U.S.C. 154(b) by 481 days.

(21) Appl. No.: 14/241,216

(22) PCT Filed: Oct. 9, 2012

(86) PCT No.: PCT/EP2012/004222
§ 371 (c)(1),
(2) Date: Feb. 26, 2014

(87) PCT Pub. No.: WO2013/053460
PCT Pub. Date: Apr. 18, 2013

(65) Prior Publication Data
US 2014/0255945 A1    Sep. 11, 2014

Related U.S. Application Data

(60) Provisional application No. 61/545,264, filed on Oct. 10, 2011.

(30) Foreign Application Priority Data

Oct. 10, 2011 (EP) .................................... 11008175

(51) Int. Cl.
*B01J 19/00* (2006.01)
*B01L 7/00* (2006.01)
(Continued)

(52) U.S. Cl.
CPC ............. *B01J 19/0013* (2013.01); *B01L 7/52* (2013.01); *C12Q 1/6844* (2013.01); *G01K 13/12* (2013.01);
(Continued)

(58) Field of Classification Search
CPC ............................. B01J 19/0046; B01J 19/00
(Continued)

(56) References Cited

U.S. PATENT DOCUMENTS 6,852,986 B1    2/2005   Lee et al.
7,188,001 B2 *  3/2007   Young ....................... B01L 7/52
                                                            422/105

(Continued)

FOREIGN PATENT DOCUMENTS

EP        2 108 942 A1    10/2009

*Primary Examiner* — Christine T Mui
(74) *Attorney, Agent, or Firm* — Saliwanchik, Lloyd & Eisenschenk

(57) ABSTRACT

The present invention relates to a calibration device and method for use in calibrating a thermal cycler having a reaction zone (140), an excitation light source (120) and an optical detector (110), the device comprising one or more ambient condition sensors (210", 230"), each adapted to sense an ambient condition at a respective position within said reaction zone, one or more emission light generators (220") adapted to be in optical communication with the optical detector (110), and control circuitry coupled to the one or more ambient condition sensors and to the one or more emission light generators, wherein the control circuitry is configured to alter the emission light generated by the one or more emission light generators based on the ambient condition sensed by the one or more ambient condition sensors.

18 Claims, 12 Drawing Sheets

(51) Int. Cl.
*G01N 21/27* (2006.01)
*G01N 21/64* (2006.01)
*C12Q 1/6844* (2018.01)
*G01K 13/12* (2006.01)

(52) U.S. Cl.
CPC ........... G01N 21/274 (2013.01); G01N 21/64 (2013.01); G01N 21/6452 (2013.01); *B01L 2200/147* (2013.01); *B01L 2200/148* (2013.01)

(58) Field of Classification Search
USPC .............................. 422/50, 68.1; 42/50, 68.1
See application file for complete search history.

(56) References Cited

U.S. PATENT DOCUMENTS

2009/0068668 A1* 3/2009 Duer .................... G01N 21/648
435/6.12
2011/0160073 A1 6/2011 Kordunsky et al.

* cited by examiner

CALIBRATION DEVICE FOR A THERMAL CYCLER

CROSS REFERENCE TO A RELATED APPLICATION

This application is a National Stage Application of International Application Number PCT/EP2012/004222, filed Oct. 9, 2012; which claims priority to European Patent Application 11 008 175.9, filed Oct. 10, 2011; and claims the benefit of U.S. Provisional Application No. 61/545,264, filed Oct. 10, 2011, all of which are incorporated herein by reference in their entirety.

FIELD OF THE INVENTION

The present invention relates to a calibration device for a thermal cycler, in particular, for a (q)PCR cycler, an HRM module, an RM module or an optical temperature reader.

BACKGROUND OF THE INVENTION

Thermal cyclers are common devices in chemical, in particular, in biochemical laboratories. They are, e.g., used to facilitate a variety of processes for creation and/or detection of molecules like, i.e., nucleic acid sequences for research, medical or industrial purposes. Processes that can be performed with thermal cyclers include, but are not limited to, amplification of nucleic acids using procedures such as the polymerase chain reaction (PCR), real-time polymerase chain reaction ((q)PCR), ligation chain reaction (LCR), high resolution melting curve (HRM) evaluation and melting curve (RM) investigation. In particular, amplification processes are used to increase the amount of a target sequence present in a nucleic acid sample while in real-time PCR, the change in amplicon amounts is monitored. Further, with HRM and MC, the denaturation or re-naturation of specific amplicons, targets or molecules may be monitored.

In order to detect the amount of a desired target sequence achieved in the samples, fluorescent labels may be used. Fluorescent labels are substances which are capable of absorbing light and emitting a light signal at a different wavelength. Some types of fluorescent labels are active in the presence of a target sequence, such that a fluorescence response from a sample is indicative of the presence and amount of the target sequence. Commonly, in order to monitor the amount of a desired target sequence, the samples are removed from the thermal cycler and put into an excitation light beam. As such a mode of detection implies that the sample is removed from the thermal cycler, e.g. US-2011/0160073 A1, in contrast, suggests to use a movable fluorescence detection module which is put on top of a thermal cycler. The detection module comprises an excitation light generator and an emission light detector that are attached to a shuttle movably mounted on a support structure. Hence, the excitation light generator and emission light detector may conveniently be positioned over the individual sample wells of the thermal cycler to detect the fluorescence response on line, i.e. during the temperature cycling.

However, with the thermal cycler comprising a large reaction zone with a plurality of sample wells, the temperature may be different in different sample wells. As the temperature severely influences the processes inside the samples, reaction rates may be different in different sample wells. It is thus desirable to investigate the spatial temperature distribution within a reaction zone of the thermal cycler. Further, it is desirable to control the heating of the reaction zone of the thermal cycler, such that a desired temperature is achieved in individual sample zones. In addition, it is desirable to provide a way to check if the optics, the optical detector and/or the excitation light source of the thermal cycler are correctly positioned, aligned and functional for each individual sample position and to provide calibration information for any occurring misalignment.

In EP 2 108 942 A1, a system for the optical detection of light from analytical samples is disclosed. The system comprises an analytical instrument comprising an optical detection unit and a sample block unit. The system further comprises a calibration device for calibrating the optical detection unit of the analytical instrument. The calibration device comprises an electrically powered reference light source emitting light that is detected by the optical detection unit. Moreover, in U.S. Pat. No. 6,852,986 B1, a fluorometer is disclosed that is combined with a thermal cycler. The fluorometer features a light emitting diode having a one-to-one correspondence to each of the plurality of sample containers, such as capped PCR tubes in a standard titer tray. The fluorometer further comprises an optical path between each LED and its correspondingly positioned container, and another optical path between each fluorescing sample within the positioned container and an optical signal sensing means.

SUMMARY OF THE INVENTION

This object is solved by a calibration device for use in calibrating a thermal cycler according to claim 1, a thermal cycler according to claim 11, a method for use in calibrating a thermal cycler according to claim 13 and machine-readable media according to claims 15 and 16. Preferred embodiments are defined in the dependent claims.

In a first aspect, the present invention provides a calibration device for use in calibrating a thermal cycler having a reaction zone, an excitation light source and an optical detector. The calibration device comprises one or more ambient condition sensors, each adapted to sense an ambient condition at a respective position within said reaction zone, one or more emission light generators adapted to be in optical communication with the optical detector and control circuitry coupled to the one or more ambient condition sensors and to the one or more emission light generators. Further, the control circuitry is configured to alter the emission light generated by the emission light generators based on the ambient condition sensed by the one or more ambient condition sensors.

The calibration device is, in particular, adapted to be used in a thermal cycler having means for real-time fluorescence detection. Such thermal cyclers are commonly equipped with an excitation light source and an optical detector. The calibration device of the invention makes use of the optical detector already present in the thermal cycler by transmitting an emission light signal to the optical detector that is indicative of the sensed ambient condition. Thus, no additional data interface is needed between the calibration device and the thermal cycler. Moreover, with the emission light generators of the calibration device being present within the reaction zone, also information about the position at which the ambient condition was sensed is transmitted to the thermal cycler. This further allows to generate a mapping of the ambient condition within the reaction zone, especially in embodiments in which the calibration device comprises more than one ambient condition sensor. For detecting the emission light generated at different positions within the reaction zone, the same means may be used as for fluorescence detection. For some thermal cyclers, this may imply that the optical detector is movably mounted within the thermal cycler such that it may detect emission light generated at different positions within the reaction zone. Alternatively or additionally, the thermal cycler may further comprise one or more mirrors and/or one or more lenses by which the emission light generated in the reaction zone is guided to the optical detector. At least one of the one or more mirrors and/or lenses may be adjustable, such that by adjusting a position and/or an inclination of the mirror and/or lenses emission light generated at different positions within the reaction zone is guided to the optical detector. The thermal cycler may further comprise means for adjusting an output signal of the optical detector based on the detected emission light and/or based on the position from which the emission light originates. The means for adjusting may, e.g. comprise an algorithm incorporated in software and/or hardware. In some embodiments, the means comprises a microcontroller which is preferably equipped with a programmable memory. The programmable memory may, e.g. comprise an EPROM or an EEPROM. Hence, the output of the optical detector is calibrated according to the detection results obtained by using the calibration device.

The calibration device of the present invention may be used to calibrate a common thermal cycler having an optical detector. To this effect, the calibration device may be sold or shipped independently from a thermal cycler or parts thereof. For example, the calibration device allows calibration of a thermal cycler which may already be present in a laboratory without requiring a hardware upgrade of the thermal cycler like, for example, by providing an additional hardware interface. In contrast, the optical detector which is anyway present in most thermal cyclers is used to receive an optical signal from the one or more emission light generators of the calibration device at the thermal cycler. Hence, no hardware modification on the side of the thermal cycler is needed.

The one or more emission light generators may, for example, be adapted to be in optical communication with the optical detector by arranging the one or more emission light generators to render a straight light path from the one or more emission light generators to the optical detector. In some instances, the calibration device further comprises means for guiding and/or modifying the emission light generated by the one or more emission light generators like, for example, one or more mirrors, lenses, etc. The one or more emission light generators may be generally arranged such that light generated by the one or more emission light generators passes to the optical detector of the thermal cycler, by which it may then be detected.

The ambient condition sensor of the calibration device may be adapted to sense any kind of ambient condition at a position within the reaction zone. The ambient condition may, for example, be a condition that may influence a physical, chemical and/or biological process or reaction within the reaction zone. The ambient condition may comprise, for example, a temperature, humidity, light, in particular excitation light irradiated into the reaction zone from the outside, concentration of a substance, etc. In embodiments, in which the ambient condition sensor comprises an excitation light sensor, the ambient condition sensor may e.g. be adapted to sense an intensity of excitation light, a luminosity, a luminescence, an intensity of illumination, one or more wave lengths, a spectrum, a subspectrum or any other physical characteristics of the excitation light.

In some embodiments, the calibration device comprises one emission light generator and one ambient condition sensor. However, it is more preferred that the calibration device comprises a plurality of emission light generators and/or a plurality of ambient condition sensors. The number of emission light generators may be the same as the number of ambient condition sensors. In this embodiment, there may be a one-to-one correspondence between an ambient condition sensor and a respective emission light generator. The emission light generated by the emission light generator may thus be indicative of an ambient condition sensed by the corresponding ambient condition sensor. Alternatively, more than one ambient condition sensors may correspond to an emission light generator. The emission light may, e.g. be altered based on an average or a median of the ambient conditions sensed by the ambient conditions sensors.

In embodiments with more than one emission light generators, the control circuitry may be configured to alter the emission light generated by more than one emission light generators based on an ambient condition sensed by one of the one or more ambient condition sensors or based on an average ambient condition sensed by two or more of the ambient condition sensors. In this embodiment, identical signals are generated by a plurality, preferably by all of the emission light generators. Differences in emission light detected by the optical detector of the thermal cycler are thus indicative of imperfections of the optical detector or the optics associated with the optical detector like, e.g. lenses, mirrors, etc. The detected emission light can thus be used to calibrate the output signal of the optical detector for different positions in the reaction zone. In some embodiments, the control circuitry is configured to alter the emission light of each emission light generator based on the ambient condition sensed by any ambient condition sensor according to a user selection.

In some embodiments, the calibration device further comprises a device memory adapted to store a parameter being indicative of the sensed ambient condition. The device may, e.g. store the parameter at regular time intervals for a predetermined period of time. In some embodiments, the device is configured to store one or more parameters in the device memory, each parameter being indicative of an ambient condition sensed by one of the ambient conditions sensors or being indicative of an average ambient condition. Generally, the term average ambient condition may refer to a time average of an ambient condition sensed by a single ambient condition sensor and/or an average of ambient conditions sensed by two or more ambient condition sensors.

The calibration device may further be dimensioned to fit into the reaction zone of a standard thermal cycler. The device may thus be conveniently used to calibrate a known thermal cycler before starting operation or in some regular intervals during use. In some embodiments, the calibration device has a substantially rectangular, in particular, a substantially quadratic layout. This is especially preferred when the calibration device is used with a thermal cycler having a rectangular or quadratic block of sample wells. In some embodiments, the calibration device may be dimensioned to extend across the entire reaction zone of the thermal cycler. Alternatively, the calibration device may be dimensioned to extend across a portion of the reaction zone. In some embodiments, the calibration device further comprises means for attaching the device to the thermal cycler like, e.g., clamping means, screws and/or an adaptor.

The emission light generator may, for example, comprise one or more light emitting diodes (LEDs). In some embodiments, the calibration device further has a power interface to be connected with the thermal cycler or a power outlet. Additionally or alternatively, the calibration device may comprise a battery.

The one or more emission light generators are adapted to be in optical communication with the optical detector of the thermal cycler, i.e., they are arranged such that the emission light generated by the emission light generator is emitted in the direction of the optical detector. In some embodiments, this may comprise one or more optical elements being arranged in the emission light path between the emission light generators and the optical detector like, for example lenses or filters. Such optical elements may be comprised by the calibration device and/or by the thermal cycler.

In some embodiments, the control circuitry is configured to alter the emission light generated by the one or more emission light generators by adjusting a spectrum and/or a dose of the emission light, in particular, by adjusting an emission light turn-on duration and/or an emission light intensity. The emission light intensity may be adjusted and/or calibrated, e.g. by adjusting an electric power provided to the emission light generators. The electric power may be provided to the emission light generator, for example by direct current (DC), direct voltage, pulse-width modulation (PWM) or amplitude modulation. In embodiments, in which the emission light is provided in a pulsed way, the turn-on duration may refer to a period of time that comprises a plurality of pulses. Altering the emission light generated by the emission light generator may, for example, comprise altering a current amplitude, a voltage amplitude, a duty cycle of a current or voltage, and/or a pulse repetition rate. This way, the intensity of the generated emission light may be altered. Generally, by altering the intensity of the generated emission light, also other parameters of the emission light like, e.g. the irradiance, flux density and radiance are altered. Throughout this disclosure it is to be understood that altering an emission light intensity is equivalent to altering any of these emission light parameters.

In some embodiments, the control circuitry is configured to increase the turn-on duration and/or the intensity of the emission light generated by the emission light generator when a parameter of the ambient condition sensed by the one or more ambient condition sensors has increased. Alternatively, the control circuitry may be configured to decrease the turn-on duration and/or the intensity of the emission light generated by the emission light generator when a parameter of the sensed ambient condition has increased. In some embodiments, the control circuitry is configured to alter the turn-on duration and/or the intensity of the emission light depending on and, in particular, proportionally to a parameter of the sensed ambient condition. In some embodiments, the control circuitry is configured to alter the emission light by modulating the emission light in a sequential way, e.g. in the shape of a binary code indicating the sensed ambient condition. The thermal cycler may be configured to evaluate the binary code to obtain the sensed ambient condition.

Alternatively or additionally, the control circuitry may be configured to alter a spectrum of the emission light based on the sensed ambient condition. In particular, the control circuitry may be configured to increase an intensity of a first wavelength of the emission light and to decrease an intensity of a second wavelength of the emission light when a parameter of the ambient condition has changed, i.e. when the parameter has decreased or increased.

According to a preferred embodiment, the one or more ambient condition sensors comprise one or more temperature sensors and/or one or more excitation light sensors.

With the ambient condition sensors comprising temperature sensors, the temperature within the reaction zone of the thermal cycler may be monitored. The emission light generated by the emission light generators may then be based on the temperature in the reaction zone. With more than one temperature sensor, the temperature distribution at different positions within the reaction zone may be monitored. The light generated by the emission light generator is received by the optical detector of the thermal cycler. The thermal cycler may then store the temperature information for later use, e.g. in controlling a heater of the thermal cycler adapted to heat the reaction zone, in controlling an excitation light source and/or in adjusting an output signal of the optical detector. In particular, storing the temperature information may comprise storing a parameter indicative of the emission light detected by the optical detector.

Alternatively or additionally, the ambient condition sensors may comprise one or more excitation light sensors. Thermal cyclers for real-time fluorescence detection are commonly equipped with an excitation light source. The excitation light generated by the excitation light source is guided to the reaction zone of the thermal cycler in order to stimulate fluorescence and to thereby monitor the amount of a target sequence. However, the different light paths from the excitation light source to the various sample wells may lead to different intensities of the excitation light at different positions within the reaction zone. With the ambient condition sensors of the calibration device comprising excitation light sensors, the excitation light distribution may be monitored at different positions within the reaction zone.

The sensed excitation light is sensed by the calibration device and one or more parameters of the sensed excitation light may be stored in the calibration device, e.g. in a device memory, for later use. The stored parameter may be used for calibrating and/or adjusting the excitation light source, optics and filters of the thermal cycler. This generally leads to a more precise evaluation of the amount of target sequence in different sample wells within the reaction zone.

The sensed excitation light intensity and/or spectrum may then be transmitted to the optical detector of the thermal cycler via the emission light generators of the calibration device. Hence, the thermal cycler may generate a map of the excitation light intensity at different locations within the reaction zone. This information may be used for calibrating and/or adjusting the emission light detected by the optical detector of the thermal cycler. This generally leads to a more precise detection of the amount of target sequence in different sample wells within the reaction zone. Alternatively or additionally, the excitation light sensor may be adapted to sense a spectrum of incoming excitation light. This may comprise, e.g., the excitation light sensor sensing the intensity of the incoming excitation light at different wavelengths. Hence, dispersion effects due to imperfect optical elements of the thermal cycler may be detected and accounted for. The control circuitry may be configured to alter the emission light based on a spectrum of the incoming excitation light. This may comprise, e.g. modulating the emission light according to a binary code based on the sensed spectrum.

Most preferably, the ambient condition sensors comprise one or more temperature sensors and one or more excitation light sensors. The calibration device may then be conveniently used to monitor, both, the temperature and the excitation light intensity within the reaction zone. The sensed temperatures and/or excitation light intensities may be fed back to the thermal cycler.

In a preferred embodiment, the control circuitry is configured to be switched by a user to at least one, preferably to each of the following modes of operation: A mode A, wherein the control circuitry is configured to store one or more temperatures sensed by one or more temperature sensors, a mode B, wherein the control circuitry is configured to alter the emission light based on one or more temperatures currently sensed by one or more temperature sensors, a mode C, wherein the control circuitry is configured to alter the emission light based on an average of one or more temperatures sensed by one or more temperature sensors, and a mode D, wherein the control circuitry is configured to alter the emission light based on excitation light sensed by one or more excitation light sensors.

In some embodiments, the calibration device further has a switch coupled to the control circuitry. The control circuitry may then be configured to alter the emission light based on the temperature when the switch is in a first position and to alter the emission light based on the sensed excitation light intensity when the switch is in a second position. The switch may, in particular comprise an electrically and/or a mechanically actuated switch like, e.g. a switchpanel. In this embodiment, the user may conveniently choose whether to calibrate the thermal cycler for temperature, optical detector optics, excitation light optics and/or any combination thereof.

According to a preferred embodiment, the calibration device further comprises an interface for transmitting signals indicating the sensed ambient condition. The device may be configured to transmit a parameter stored in a device memory via the interface. The interface may, in particular, comprise an electric connection like, for example, a cable or a socket and/or a wireless communication adapter. The interface may be adapted for communication, e.g. with electric components of an external computer and/or with the thermal cycler. In this embodiment, the sensed ambient condition is not only transmitted to the thermal cycler via the emission light generators, but may also be transmitted to the thermal cycler or to an external device by other means. The transmitted information may, in particular be useful for postprocessing assessment of reaction results in the samples.

According to a preferred embodiment, the one or more ambient condition sensors and the one or more emission light generators are arranged together in pairs. Hence, each emission light generator may be adapted to generate emission light based on the ambient condition of the associated sensor. Arranging a sensor and a light generator in a pair may, in particular, comprise that the sensor and the generator are arranged close to each other. In some embodiments, the sensor and the light generator of the pair may be arranged in an overlapping arrangement. In embodiments, in which the calibration device further comprises a planar carrier, this may comprise that the sensor and the light generator of the pair are arranged at substantially a same position on opposite sides of the carrier.

According to a preferred embodiment, the calibration device further comprises a substantially planar carrier with top and bottom sides, wherein the one or more emission light generators are located on the top side of the carrier. This is especially useful for thermal cyclers comprising a plurality of sample wells. The carrier may be positioned on top of the sample wells, such that the emission light generators are facing towards the optical detector. It is even more preferred that the one or more ambient condition sensors comprise one or more temperature sensors arranged on the bottom side of the carrier. With an arrangement of the temperature sensors and the emission light generators on opposite sides of the carrier, the light generators may be positioned substantially at the same position as the temperature sensors. Hence, the emission light may be generated at substantially the same position at which the temperature is sensed, giving rise to a more precise monitoring of the temperature distribution within the reaction zone.

It is even more preferred that the temperature sensors are arranged on protrusions on the bottom side of the carrier. The protrusions may be further configured to fit into sample wells within the reaction zone of the thermal cycler. Hence, the temperatures may be sensed within the sample wells, i.e. at the positions where the desired reactions take place. The temperature sensors may, in particular, be arranged at the top of the protrusions. In some embodiments, the protrusions have a length of between 5 mm and 50 mm, in particular, of between 5 mm and 40 mm, and, preferably, of between 5 mm and 20 mm. In some embodiments, the protrusions are cylindrical or conical. The protrusions may, for example, have a maximum outer diameter of between 1.5 mm and 15 mm, in particular, of between 1.5 mm and 12 mm, and, preferably, of between 2 mm and 10 mm. In some embodiments, the protrusions comprise a flexible material like, for example, rubber. Hence, the walls of the reaction zone or the sample wells will not be damaged when the calibration device is installed in the thermal cycler. The protrusions and/or the temperature sensors may be waterproof. This is especially useful, if the user wants to monitor the temperature when liquid is inserted in the sample well. As the thermal conductivity of the liquid is higher than that of air, this would allow for a more precise monitoring of the temperature inside the samples.

In a preferred embodiment, the ambient condition sensors comprise one or more excitation light sensors and one or more excitation light filters positioned in the light path of the one or more excitation light sensors. This allows to adjust the calibration device for different excitation light wavelengths generated by the excitation light source of the thermal cycler. In particular, the one or more excitation light filters may comprise a plurality of filter wavelengths. Hence, the excitation light may be monitored with regard to different excitation wavelengths. In some embodiments, the excitation light filters are removable. The user may thus replace the excitation light filters by filters that correspond to the excitation light source of the thermal cycler. Additionally or alternatively, each excitation light sensor may be associated with a corresponding excitation light filter. Hence, the filters may be individually configured for monitoring the excitation light distribution at a specific position within the reaction zone.

In embodiments, in which the calibration device comprises a carrier with top and bottom sides, the one or more excitation light sensors may, in particular, be arranged on the top side of the carrier. This is preferred as for common thermal cyclers, the excitation light source is arranged on the same side as the optical detector.

According to a preferred embodiment, the calibration device further comprises one or more emission light filters positioned in the light path of the one or more emission light generators. The emission light filters may be used to adjust the calibration device to a specific optical detector used in the thermal cycler. The emission light filters may, in particular, be removable. Hence, the user may choose emission light filters that correspond to the optical detector in the thermal cycler. It is even more preferred that each emission light generator is associated with a corresponding emission light filter. This allows to arrange the emission light filter in the proximity of the corresponding emission light generator, allowing for a higher precision of ambient condition monitoring within the reaction zone. In particular, the emission light filters and/or the excitation light filters may be arranged in a cover of the calibration device. In embodiments, in which the calibration device comprises a carrier, the cover may, in particular, be arranged on the top side of the carrier. The cover may be adapted to prevent damage to the calibration device caused by mechanical shocks. In some embodiments, the calibration device is waterproof.

The excitation light filters and/or emission light filters may be substantially circular. In some embodiments, the emission light filter and/or excitation light filter may have a diameter of between 2 mm and 15 mm, in particular, between 4 mm and 12 mm and, preferably, between 5 mm and 10 mm. The excitation light filters may correspond to wavelengths in the range of 320 nm to 750 nm, preferably of 320 nm to 500 nm. The choice of filter wavelength may be based on the desired application. The emission light filters may correspond to wavelengths in the range of 320 nm to 750 nm, preferably of 350 nm to 720 nm.

The cover of the calibration device may be made of plastic. In particular, the cover may comprise a non-reflecting top side to avoid reflection of the excitation light. The carrier may comprise a metal like, for example, copper or aluminum. Alternatively or additionally, the carrier may comprise plastics. In some embodiments, the carrier comprises a printed circuit board (PCB).

In a second aspect, the present invention provides a thermal cycler comprising a reaction zone, an optical detector and a calibration device of the aforementioned kind. In particular, the calibration device may be removably arranged in the reaction zone. The thermal cycler may further comprise a support structure to which the optical detector and the calibration device are attached.

According to a preferred embodiment, the thermal cycler further comprises an excitation light source adapted to generate excitation light directed towards the reaction zone. With such an arrangement, the thermal cycler may also be used for fluorescence detection of target sequences within the reaction zone. The excitation light may, in particular, comprise one or more discrete wavelengths and/or one or more continuous ranges of wavelengths. This allows for use of a broad range of different fluorescence labels.

In some embodiments, the thermal cycler further comprises an excitation light filter and/or an emission light filter. This allows to adapt the thermal cycler for use with specific fluorescence labels. In particular, the thermal cycler may comprise an excitation light filter wheel and/or an emission light filter wheel comprising a plurality of excitation light filters or emission light filters, respectively. Hence, the user may conveniently choose a filter of a desired wavelength corresponding to the fluorescence label contained in the sample.

According to a preferred embodiment, the thermal cycler further comprises a memory coupled to the optical detector and adapted to store a parameter detected by the optical detector and the thermal cycler further comprises a heater adapted to heat the reaction zone based on the stored parameter. In this embodiment, the temperature sensed by the calibration device may be used to control the heater of the thermal cycler. For example, when it is detected that the temperature at a position in the reaction zone is lower than a temperature value nominally expected, the heater may use this information to increase its heating power to a value higher than the nominal heating power. As the sensed temperature is converted into emission light by the calibration device, the emission light detected by the optical detector is indicative of the temperature at different positions within the reaction zone.

In a preferred embodiment, the thermal cycler comprises a memory coupled to the optical detector and adapted to store a parameter of the emission light detected by the optical detector and further comprises the optical detector being adapted to output a signal based on a currently detected emission light and on the stored parameter. In this embodiment, the emission light generated by the calibration device is indicative of a sensed excitation light. The emission light is detected by the optical detector and is stored for later use. When the thermal cycler is employed for facilitating chemical processes afterwards, the optical generator uses the stored parameter to calibrate its output. For example, when the thermal cycler, using the calibration device, detects that the excitation light intensity is low in a specific sample well, the optical detector may, for emission light generated in that sample well, output a higher result than detected. The result may, in particular, be calculated based on the detected emission light and on the stored parameter. The parameter may, e.g. comprise a turn-on duration, an intensity and/or a spectrum of the detected emission light.

In some embodiments, the optical detector is arranged on a carriage that is movably arranged. This allows to move the optical detector to different positions, such that emission light generated at different positions within the reaction zone may be detected. Additionally or alternatively, the thermal cycler may comprise one or more adjustable optical elements, in particular, one or more adjustable mirrors. In these embodiments, the mirrors may be used to guide the emission light generated at various positions within the reaction zone to the optical detector. In this case, the optical detector may be fixedly positioned relative to the reaction zone.

According to the preferred embodiment, the thermal cycler further comprises a plurality of sample wells located in the reaction zone. This allows to subject a plurality of samples to temperature cycling by the thermal cycler. The sample wells may be arranged symmetrically, for example in rows within the reaction zone.

In a third aspect, the present invention provides a method for use in calibrating a thermal cycler with a reaction zone and an optical detector, in particular, a thermal cycler of the aforementioned kind. The method comprises: sensing an ambient condition at one or more positions within the reaction zone, and generating one or more emission light beams, said emission light being indicative of the sensed ambient condition.

This corresponds to methods steps being carried out by the calibration device. According to a preferred embodiment, the step of generating said one or more emission light beams comprises generating said emission light beams in the vicinity of said one or more positions within the reaction zone. Hence, the emission light beam is indicative of the ambient condition at substantially the same position at which the light beam is generated. This leads to a higher precision of spatial monitoring of the ambient condition.

In a fourth aspect, a method to be executed by a thermal cycler having a reaction zone and a heater adapter to heat the reaction zone is provided, the method comprising: Detecting emission light generated in the reaction zone, preferably using the calibration device of the aforementioned kind, the emission light being indicative of a temperature at a position within the reaction zone, storing a parameter of said detected emission light, and controlling the heater at least partially based on the stored parameter.

With these method steps, the detected emission light indicating an ambient condition sensor at various positions within the reaction zone is stored for later use in controlling a heater of the thermal cycler. The parameter may, in particular, refer to an intensity and/or a turn-on duration of the detected emission light.

This method may be used for calibrating the thermal cycler. In particular, the temperature detected in the reaction zone may be used for calibrating the heating of the reaction zone.

The method may further comprise detecting emission light generated in the reaction zone and generating an output signal based on the detected emission light and the stored parameter. Hence, imperfections of the optical detector and the optical elements associated therewith assessed by means of the calibration device as set forth above may be used later on to calibrate and/or to adjust the output of the optical detector.

In a fifth aspect, a method to be executed by a thermal cycler having a reaction zone, an excitation light source and an optical detector is provided, the method comprising: Detecting emission light generated in the reaction zone, preferably using the calibration device of the aforementioned kind, the emission light being indicative of incoming excitation light at a position within the reaction zone, storing a parameter of said detected emission light, and providing excitation light by the excitation light source at least partially based on the stored parameter.

In this aspect, a method for calibrating the thermal cycler for non-uniform excitation light distribution within the reaction zone is provided.

In a sixth aspect, a method is provided, comprising method steps disclosed above with regard to the third, the fourth and/or the fifth aspect of the present invention.

In a seventh aspect, the invention provides a machine-readable medium containing instructions that when executed by a thermal cycler having a reaction zone and a heater adapted to heat the reaction zone, cause the thermal cycler to execute method steps of the fourth, the fifth and/or the sixth aspect of the invention.

In an eighth aspect, a kit comprising the calibration device according to the first aspect and the machine-readable medium of the seventh aspect are provided.

It is further to be understood that features and advantages disclosed with regard to one aspect may also be implied and incorporated by other aspects of the invention.

SHORT DESCRIPTION OF DRAWINGS

The invention is now described with reference to the attached drawings, wherein.

Figure 4A:
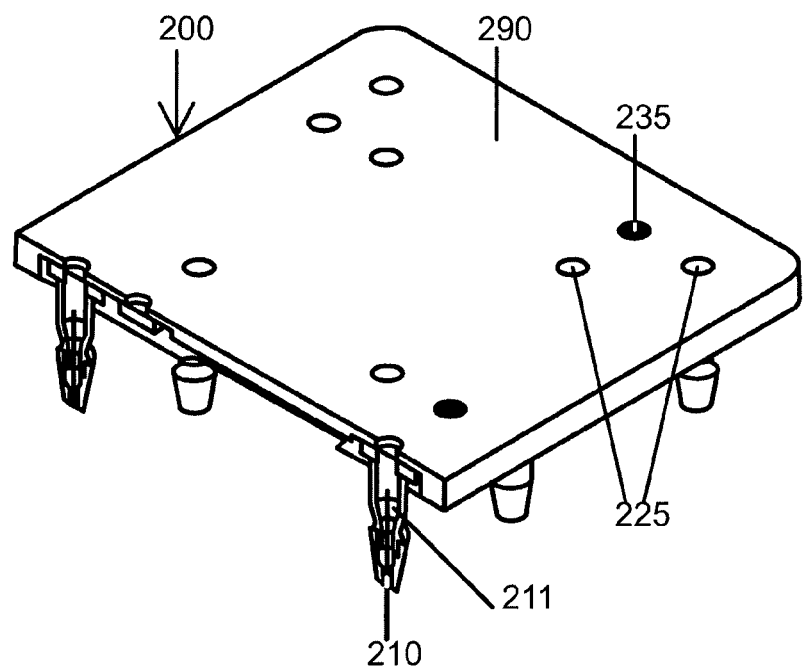
FIG. 4A shows a portion of a calibration device according to the invention.
Figure 4B:
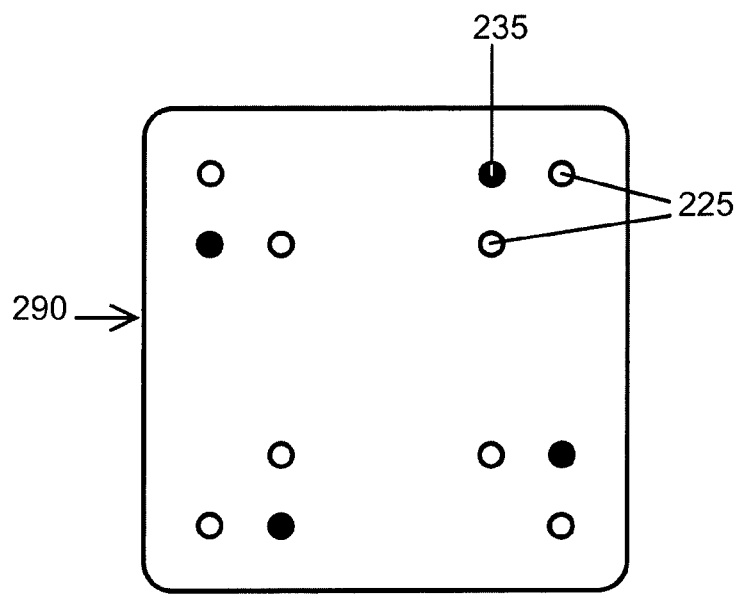
Figure 4C:
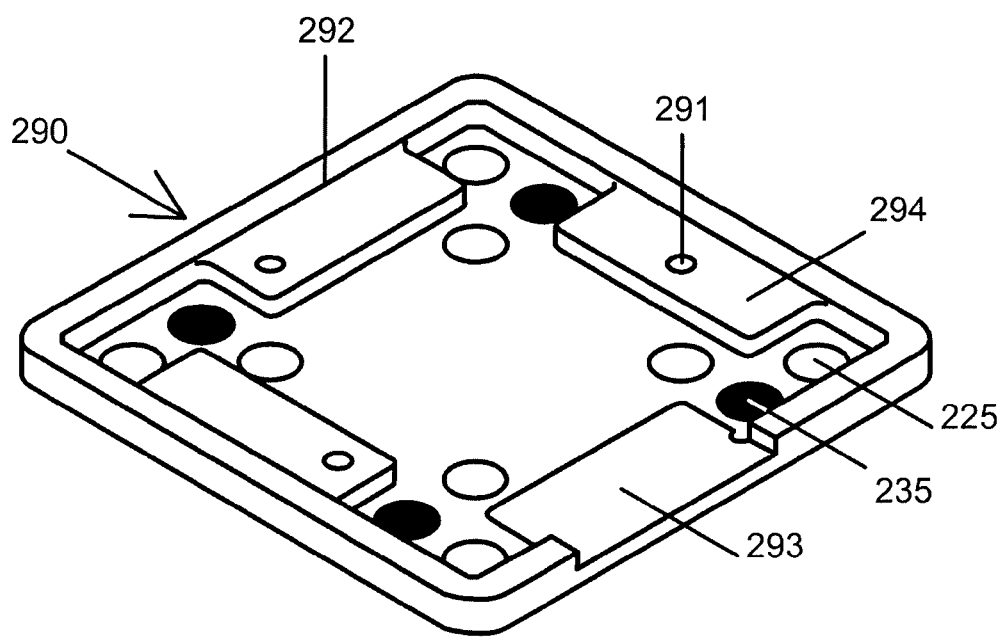
Figure 4D:
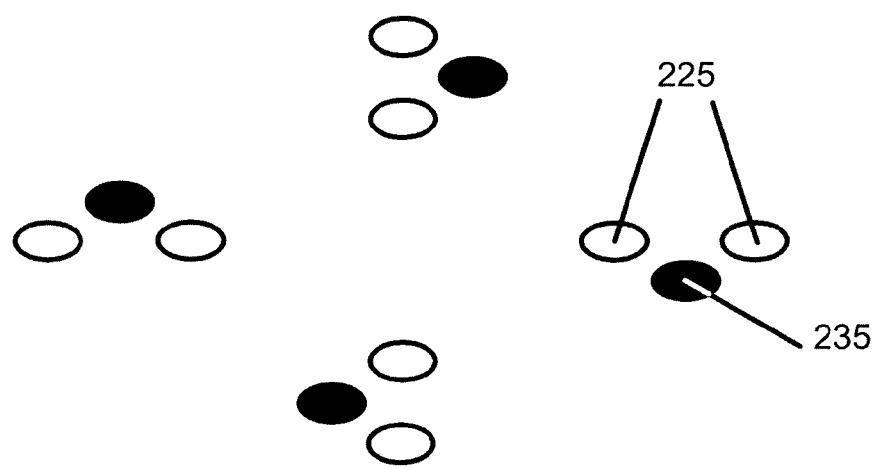
Figure 5A:
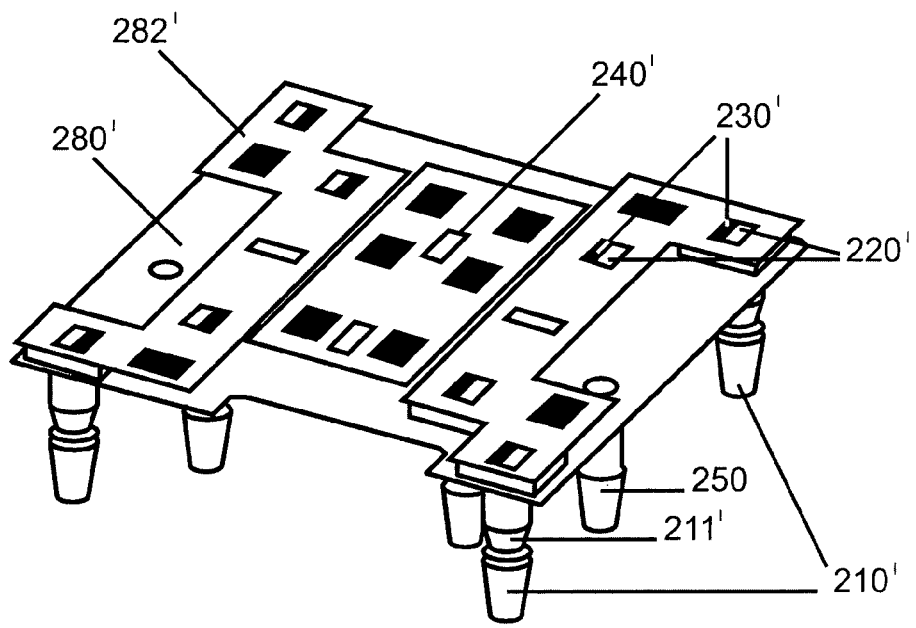
Figure 5B:
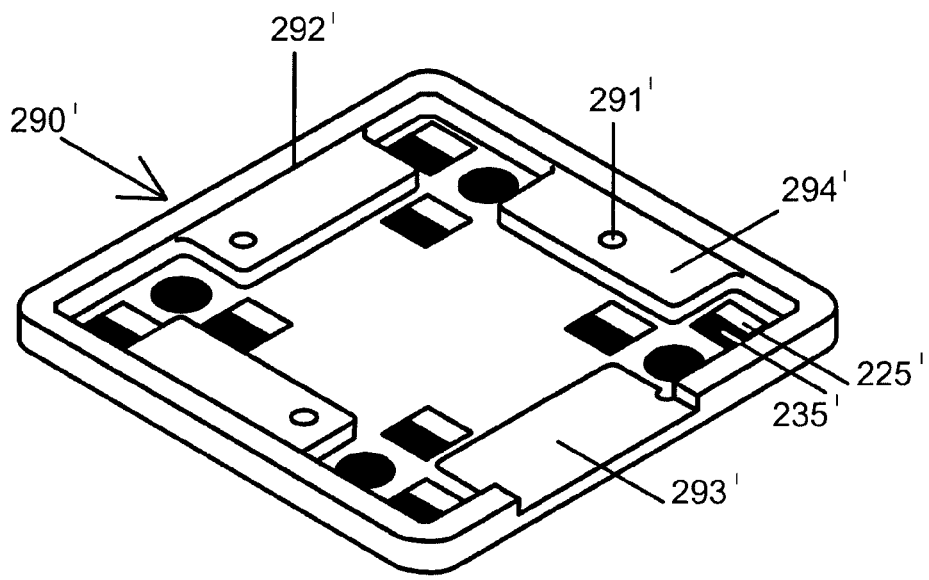
Figure 6:
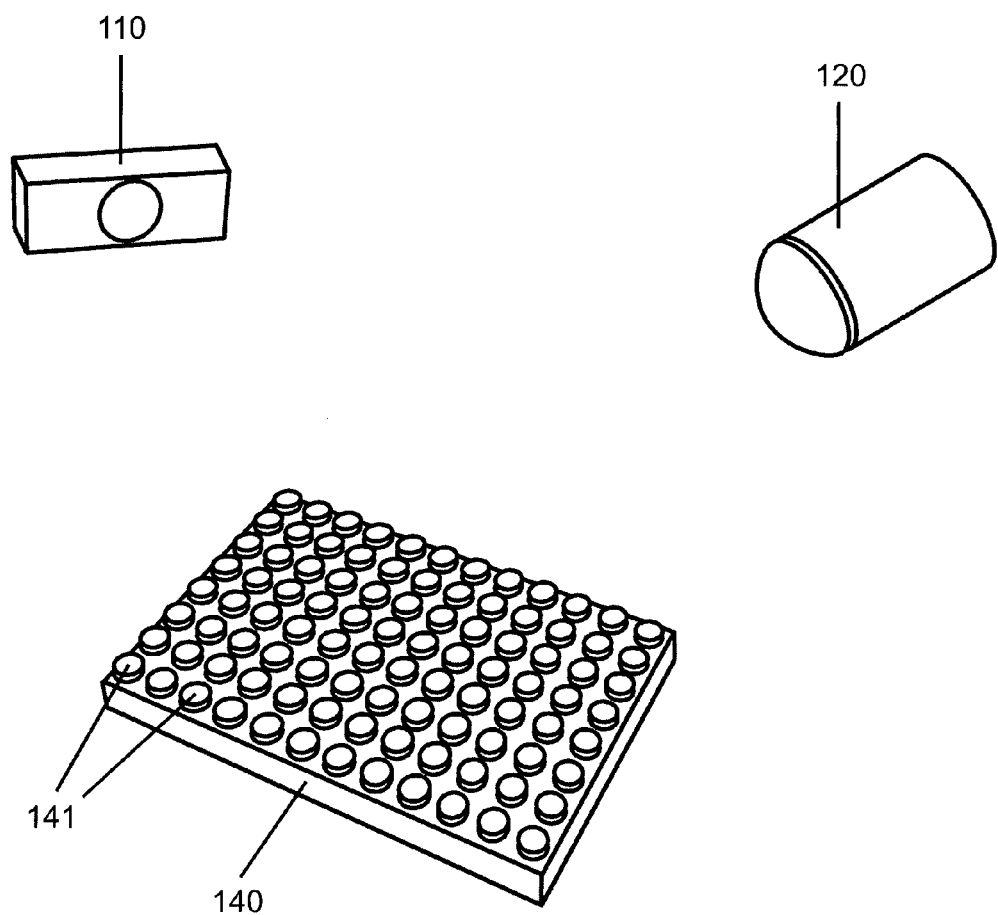
Figure 7:
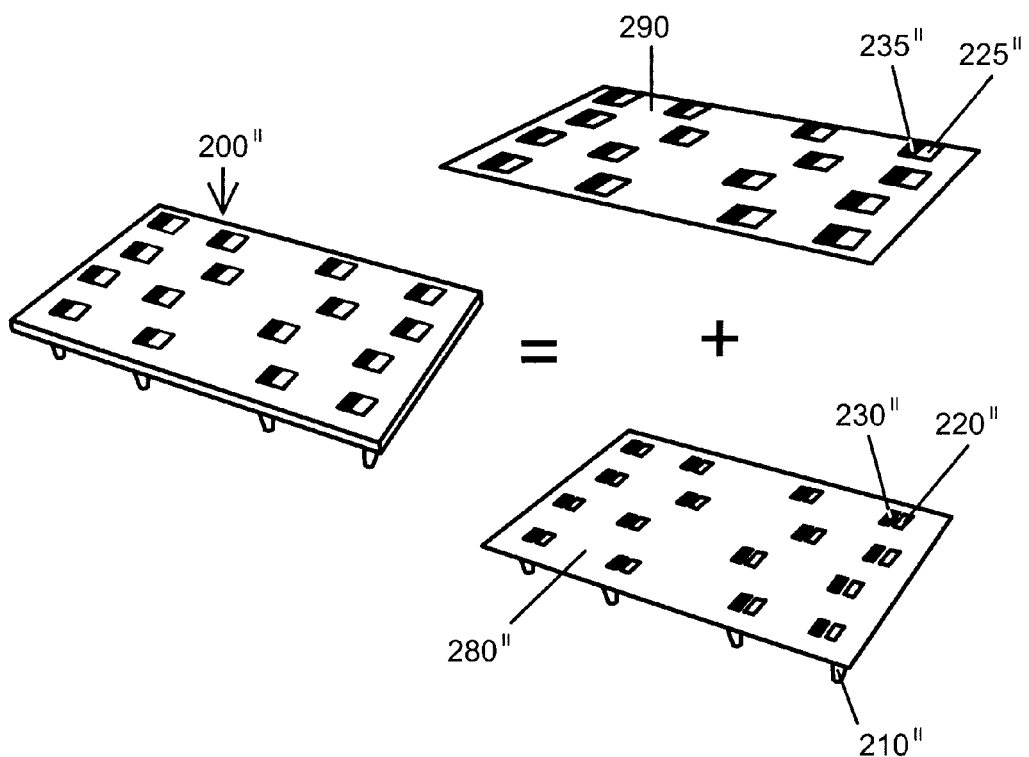
Figure 8:
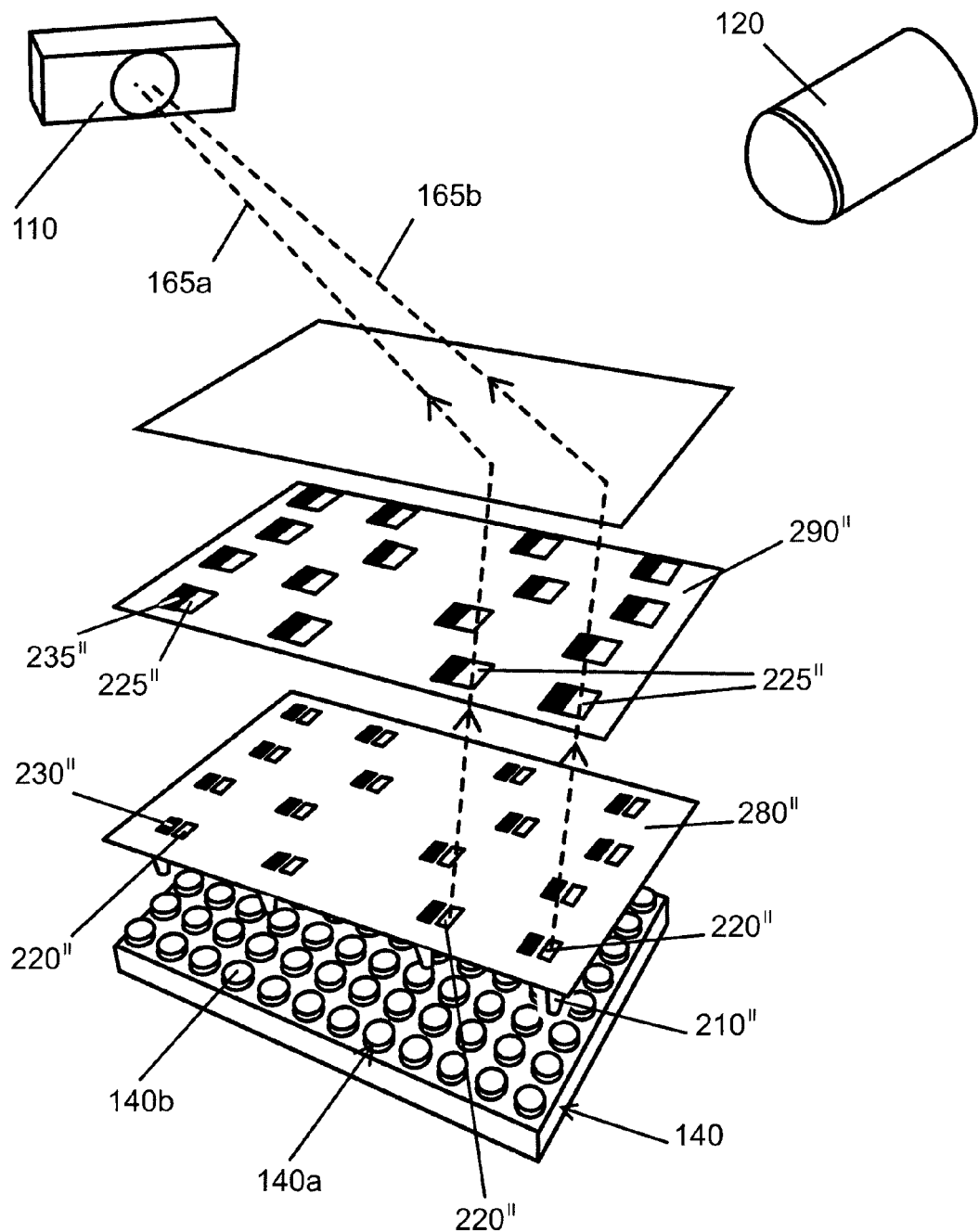
Figure 9:
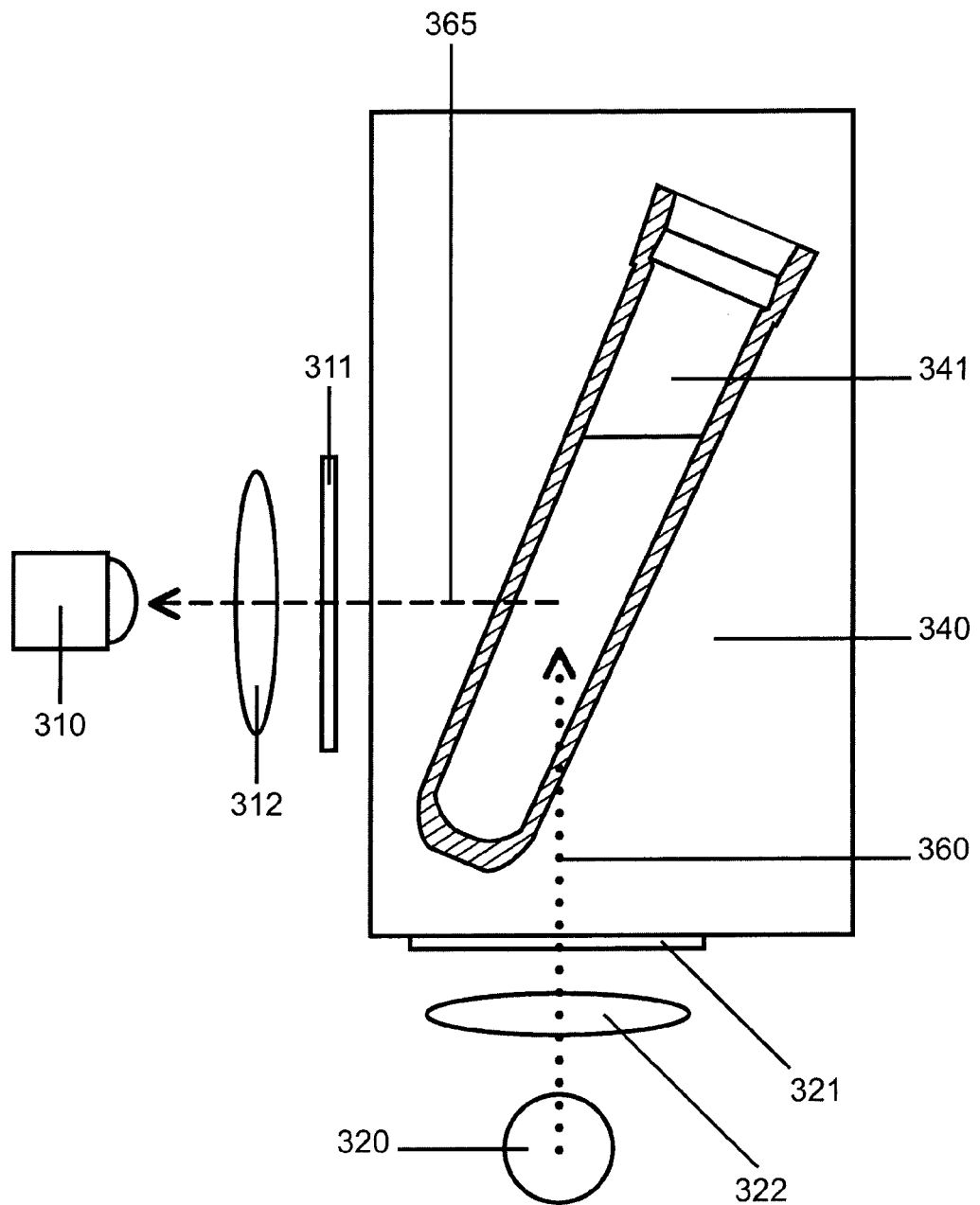
Figure 10A:
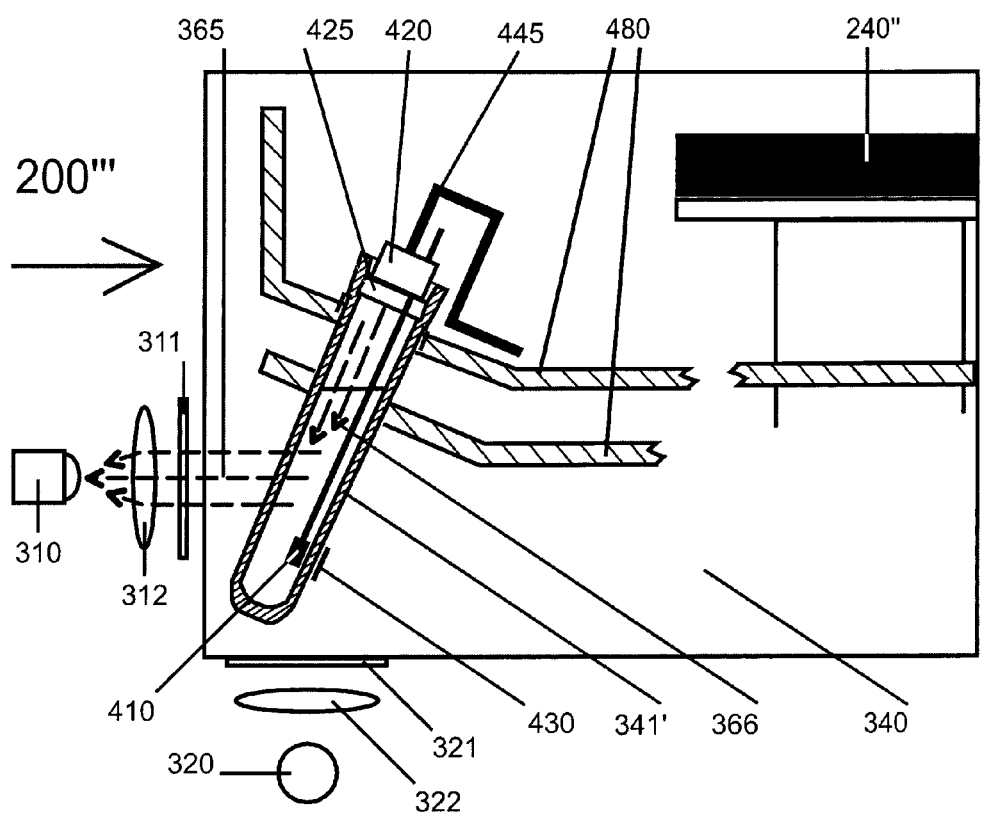

FIGS. 4B, C show the cover of the calibration device of the invention,

FIG. 4D shows excitation and emission light filters of the calibration device according to the invention, FIG. 5A shows a calibration device according to the invention without cover, FIG. 5B shows the cover of a calibration device according to the invention, FIG. 6 shows a schematic diagram of a known thermal cycler (prior art), FIG. 7 shows a calibration device according to the invention, FIG. 8 shows a schematic drawing of the calibration device according to the invention in the thermal cycler of FIG. 6, FIG. 9 shows a schematic view of a known thermal cycler (prior art), FIG. 10A shows a schematic drawing of the calibration device according to the invention installed in the thermal cycler of FIG. 9

Figure 10B:
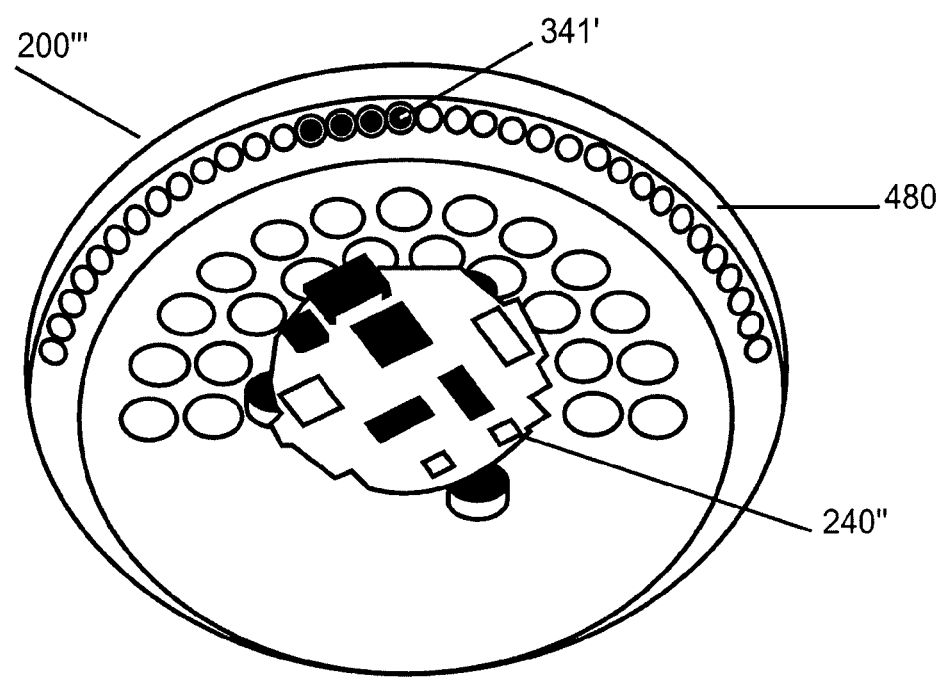

FIG. 10B shows a calibration device according to the invention as used in a known thermal cycler of FIG. 9.

DETAILED DESCRIPTION OF PREFERRED EMBODIMENTS

Figure 1:
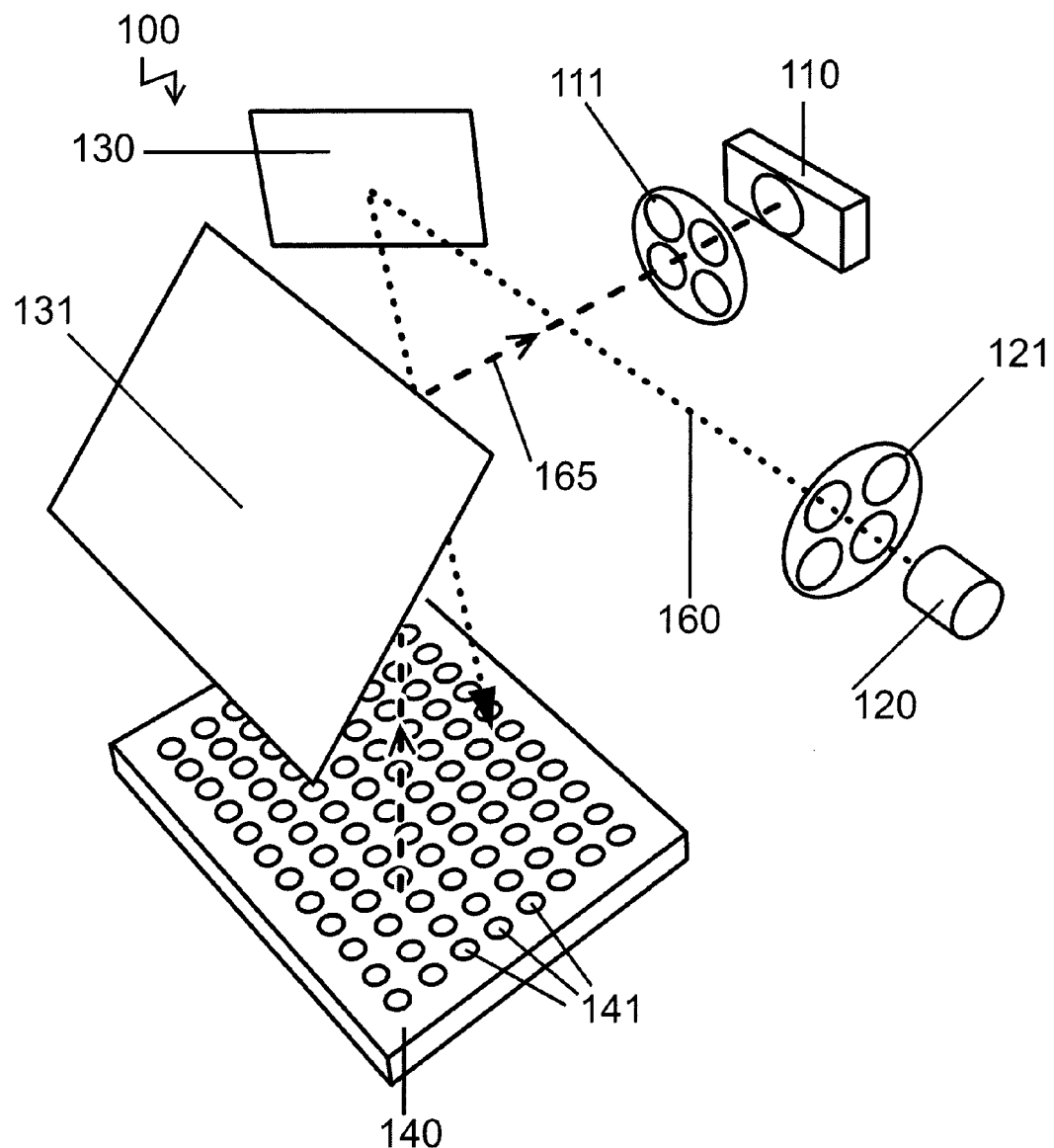
FIG. 1 shows a known thermal cycler (prior art)

FIG. 1 shows a schematic drawing of a known thermal cycler 100. Thermal cycler 100 comprises an excitation light source 120 and an excitation light filter wheel 121. The excitation light filter wheel 121 includes several excitation filters that may be moved into the excitation light beam 160 generated by the excitation light source 120 by turning the wheel 121 accordingly. The thermal cycler 100 further comprises a reaction zone with eight rows of sample wells 141, each row comprising twelve sample wells 141. The sample wells 141 are provided in a block 140 that is thermally coupled to a heater of the thermal cycler (not shown). The excitation light beam 160 is directed from the excitation light source 120 through a filter of the excitation filter wheel 121 of the thermal cycler and, from there it is guided by a mirror 130 to the sample wells 141. The mirror 130 is adjustable, such that the excitation light beam 160 may be guided to different sample wells 141.

The thermal cycler 100 further comprises an optical detector 110 and an emission filter wheel 111. An emission light beam 165 is generated by fluorescent labels contained in a sample in one of the sample wells 141 and is guided via mirror 131 towards the optical detector 110. The emission light filter wheel 111 includes several emission light filters that may be moved into the emission light beam 165 by turning the wheel 111. The thermal cycler 100 further comprises electronics (not shown in FIG. 1) that is coupled to the excitation light source 120 and to the optical detector 110. The electronics evaluates a signal generated by optical detector 110 in reaction to the incoming emission light beam 165. This way, the amount of a desired target sequence in the sample wells 141 may be monitored.

Further optical elements like, e.g. one or more lenses in the excitation and/or emission light path are omitted in FIG. 1 for clarity reasons, but may be present in the thermal cycler according to the invention.

Figure 2:
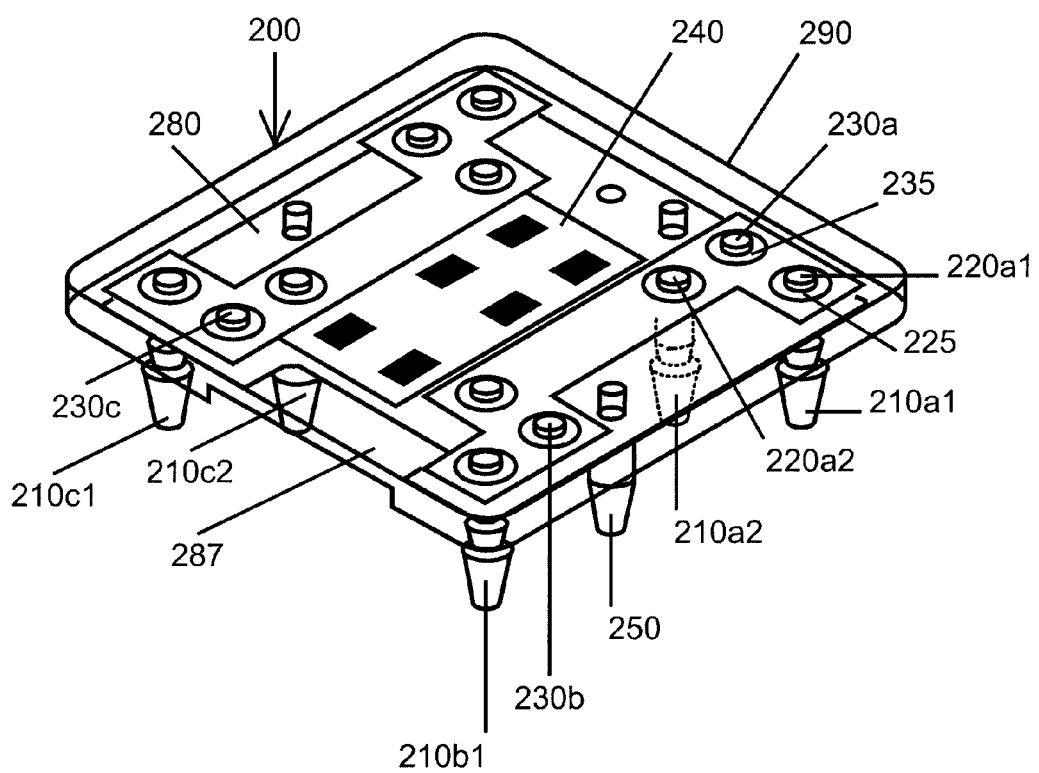
FIG. 2 shows a calibration device according to the invention.

FIG. 2 shows a calibration device 200 according to the invention. The calibration device 200 comprises a substantially quadratic planar carrier 280, which is provided with temperature sensors 210 (210a1, 210a2, 210 /1, 210c1, 210c2) on its bottom side. Further, the calibration device 200 comprises, at each of its four corners, a respective set of two emission light generators 220 (220a1, 220a2) and one excitation light sensor 230 (230a, 230b, 230c). The calibration device 200 further comprises control circuitry 240 that is attached to the top side of the carrier 280. The control circuitry 240 is coupled to the temperature sensors 210, to the excitation light sensors 230 and to the emission light generators 220 (connections not shown). The control circuitry 240 is configured to store the sensed temperatures and excitation light intensities and spectra. The control circuitry 240 is further configured to alter the emission light generated by the emission light generators 220 based on the temperature sensed by the temperature sensors 210 or based on the incoming excitation light sensed by the excitation light sensors 230. In more detail, the emission light generated by emission light generator 220a1 corresponds to the temperature sensed by temperature sensor 210a1. The user may further switch the control circuitry 240, such that the emission light generated by emission light generator 220a2 corresponds to the temperature sensed by temperature sensor 210a2 and/or to the intensity of the incoming excitation light sensed by excitation light sensor 230a. The control circuitry 240 is further configured to be switched by a user to a mode, wherein the emission light generated by the emission light generators 220a1,2 corresponds to an average temperature sensed by the temperature sensors 210a1,2. In that case, the emission light generated by the different emission light generators 220a1, 2 is identical.

The calibration device 200 further comprises a cover 290. The cover 290 serves as a protection cover in order to shield the control circuitry and other components of the calibration device 200 from environmental influences like, e.g. mechanical shock, pressure or humidity. Further, the cover 290 comprises openings, in which emission light filters 225 and excitation light filters 235 are provided. Each emission light filter 225 corresponds to an emission light generator 220, while each excitation light filter 235 corresponds to an excitation light sensor 230.

The calibration device 200 further comprises three projections 250 that are provided on the bottom side of the carrier 280. When in use, the projections 250 may be inserted into sample wells of the thermal cycler to stabilize the position of the calibration device 200 with respect to other components of the thermal cycler.

Figure 3:
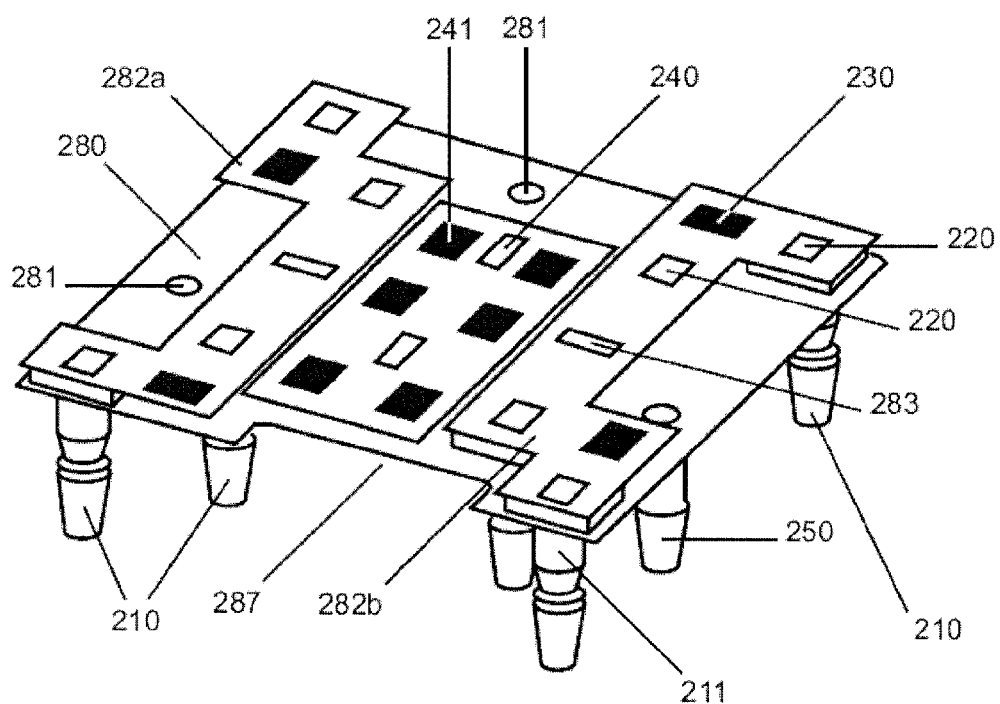
FIG. 3 shows a calibration device according to the invention without cover.

In FIG. 3, the calibration device of FIG. 2 is shown without the cover 290. In particular, the calibration device comprises a planar carrier 280. On the top side of carrier 280, two subcarriers 282a, 282b are mounted. Each subcarrier 282a, 282b extends substantially along one side of the carrier 280 and has a centrally located rectangular recess. Below the recess in the subcarrier 282a,b, a hole 281 is formed in the carrier 280. The hole 281 is thus accessible from the top, such that the carrier 280 may be attached to the protection cover 290 and to the projections 250.

Each subcarrier 282a,b comprises two sets of components, each set comprising two emission light generators 220 and one excitation light sensor 230. In particular, at each end of the subcarrier 280a, b, an emission light generator 220 is provided. For example, depending on user selection, the control circuitry 240 of the calibration device 200 alters the intensity of the emission light generated by the emission light generator 220 being located at the subcarrier 282a,b based on the temperature sensed by the temperature sensor 210 attached to the bottom side of the carrier 280. In particular, the temperature sensor 210 is attached to a protrusion 211.

Between the two subcarriers 282a,b the control circuitry 240 is mounted on the carrier 280. The control circuitry 240 comprises integrated circuits 241. In some embodiments, the control circuitry also comprises passive electric components like, for example ICs, resistors, capacitors and/or inductances.

The subcarriers 282a, 282b and/or the control circuitry 240 may be mounted on the subcarrier 280 by one or more micro-PCB connectors, by soldering, welding and/or gluing. In particular, the subcarriers 282a,b and/or the control circuitry 240 may be mounted on the carrier 280 by means of one or more micro-PCB connectors and electrically and/or thermally insulating material.

At the centre of one side of the planar carrier 280, a recess 287 is formed as shown in FIG. 3 (front side, towards the viewer). This recess 287 enables interface connection via a cable, a socket and/or wireless communication.

Each subcarrier 282a,b further comprises subcarrier electronics 283. The subcarrier electronics 283 is coupled to the emission light generators 220 and to the excitation light sensors 230 of the respective subcarrier 282a,b and, further, to the control circuitry 240 of the calibration device 200. The subcarrier electronics 283 is used to electrically interface between the emission light generator 220 and the excitation light sensors 230 of the subcarrier 282a,b, on the one side, and the control circuitry 240, on the other side. Having the emission light generators 220 together with the excitation light sensors 230 on a subcarrier separately from the control circuitry 240 allows for a modular design of the calibration device, such that different subcarriers 282a,b may be used for different thermal cyclers, while still using the same control circuitry 240. In order to electrically adapt the different emission light generators and excitation light sensors of the subcarriers to the control circuitry 240, the subcarrier electronics 283 may perform signal transformation, power conversion, etc.

In FIG. 4A, a portion of the calibration device of FIGS. 2 and 3 is shown in a perspective view. The device is cut through at a plane that extends through two temperature sensors 210 being arranged on protrusions 211. In the view of FIG. 4A, the protection cover 290 of the calibration device 200 can be partially seen in a perspective view. In FIG. 4B, the protection cover 290 of the calibration device 200 of FIGS. 2 and 3 is seen from the top. The cover 290 comprises four sets of openings, each set comprising three openings. The sets are arranged near the corners of the substantially quadratic cover 290. The three holes of each set are arranged in the corners of a right-angled triangle. In the central opening of each set, an excitation light filter 235 is provided and in the two other openings of each set, an emission light filter 225 is provided. When going from one set to another, the right-angled triangle is rotated by 90 degrees. In one set, shown in FIG. 4B top left, the excitation light filter is positioned in an opening at the bottom left position of the set. In the set shown at the top right of cover 290, the excitation light filter 235 is positioned to the top left. In the bottom left set, the excitation light filter 235 is positioned at the bottom right. In the set shown at the bottom right of the cover 290, the excitation filter is positioned in an opening at the top right. In particular, thought lines connecting the excitation light filter 235 with each of the emission light filters 225 of each set are substantially parallel to the outer edges of the cover 290. This arrangement allows to sense the temperature and excitation light in most thermal cyclers at reasonably distributed positions.

In FIG. 4C, the cover 290 of FIG. 4B is shown from the bottom. At the bottom side, the cover 290 comprises a projection 292 that runs along the outer edges of the cover 290. The projection 292 extends perpendicularly to the plane main section of the cover. At a central position on one edge, the projection 292 is interrupted. Along the interruption, a plateau 293 is formed. This plateau 293 on the bottom side of the carrier 290 corresponds to the recess formed in the carrier 280 (see FIG. 3). Similarly, the carrier 290 comprises three plateau zones 294 that are located at a central position at each of the other edges, respectively. The plateau zones 294 correspond to the recesses formed in the subcarriers 282a,b and to a section of the carrier 280 that is not covered by sub-carriers 282a,b or the control circuitry 240 (see FIG. 3). Moreover, in each of the three plateau zones 294, an opening 291 is formed which corresponds to one of the holes 281 formed in the carrier 280. A pin (not shown) may be introduced through the holes 281 in the carrier 280 and into the openings 291 in the cover 290 in order to attach the cover 290 to the carrier 280 and to the projections (cf. FIG. 3).

In FIG. 4D, the positions of the excitation light filters 235 and the emission light filters 225 of the calibration device 200 are shown. The emission light filters 225 and excitation light filters 235 are provided in the cover 290 of the calibration device 200. In total, the cover comprises four excitation light filters 235 and eight emission light filters 225.

In FIG. 5A, components of a calibration device 200' according to the invention are shown without cover 290' (cf. FIG. 5B). The calibration device comprises a carrier 280', on which control circuitry 240' is mounted in a central position on the carrier's top side. Along each longside of the control circuitry 240', a respective subcarrier 282' is mounted on the carrier 280'. The subcarriers 282' of FIG. 5 differ from the subcarriers 282a,b of FIG. 3 in that the excitation light sensors 230' and the emission light generators 220' are arranged in pairs. At each of the four corners of the carrier 280', a set of two pairs is provided, each pair comprising an excitation light sensor 230' and an emission light generator 220'.

The arrangement of temperature sensors 210' is the same as for the device illustrated by FIG. 3. In particular, the temperature sensors 210' are arranged on protrusions 211' on the bottom side of the carrier 280'. The temperature sensors 210' and the pairs of excitation light sensors 230' and emission light generators 220' are coupled to the control circuitry 240'.

In FIG. 5B, the cover 290' of the calibration device 200' of FIG. 5A is shown from the bottom. At the bottom side, the cover 290' comprises a projection 292' that extends along the outer edges of the cover 290'. The projection 292' extends perpendicularly to the plain main section of the cover 290'. At a central position on one edge, the projection 292' is interrupted. Along the interruption, a plateau 293' is formed. This plateau 293' on the bottom side of cover 290' corresponds to the recess formed the carrier 280' (see FIG. 5A). Similarly, the carrier 290' comprises three plateau zones 294' located at a central position at each of the remaining outer edges, respectively. The plateau zones 294' correspond to the recesses formed in the subcarrier 282' and to a section of the carrier 280' is not covered by subcarriers 282' or the control circuitry 240' (see FIG. 5A). Moreover, in each of the three plateau zones 294' an opening 291' is formed. A pin (not shown) may be introduced through the openings 291' and holes in the carrier 281' in order to attach the cover 290' to the carrier 280' and to the projections 210'. In addition, the excitation light filters 235' and the emission light filters 225' of the calibration device 200' are shown. The emission light filters 225' and excitation light filters 235' are provided in pairs in the cover 290' of the calibration device 200'. In total, the cover 290' comprises eight excitation light filters 235' and eight emission light filters 225'.

In FIG. 6, components of a known thermal cycler are shown in a schematic view. As in FIG. 1, the thermal cycler of FIG. 6 comprises an excitation light source 120 and an optical detector 110. The thermal cycler further comprises a reaction zone, in which a block 140 of sample wells 141 is arranged. The sample wells 141 are arranged in rows. The block 140 is thermally coupled to a heater (not shown) of the thermal cycler. The heater is configured to subject the block 140 to a temperature cycle. In particular, the thermal cycler may be configured to cycle the temperature inside the sample wells 141 between 20° C. and 100° C. In some embodiments, parameters of the temperature cycle are adjustable by a user. In particular, the user may predetermine the minimum temperature and the maximum temperature of the cycle, the heating rate, the cooling rate, the cycle period and/or a temperature profile like, for example a sinusoidal or a saw-tooth form.

In FIG. 7, the construction of a calibration device 200' according to the invention is shown. The calibration device 200" comprises a carrier 280", on which pairs of excitation light sensors 230" and emission light generators 220" are provided. The pairs are arranged on the top side of the carrier 280", while temperature sensors 210" are provided on protrusions on the bottom side of the carrier 280". In more detail, the calibration device 200" comprises 16 pairs, each pair comprising an excitation light sensor 230" and an emission light generator 220". The pairs are arranged in rows, with the pairs of each row being staggered with respect to the pairs in adjacent rows. The calibration device 200" further comprises a control circuitry (not shown in FIG. 7). Moreover, the calibration device 200" comprises a cover 290" that is attached to the top side of carrier 280". The cover 290" comprises emission light filters 225" and excitation light filters 235" which are arranged in pairs. The positions of the pairs of excitation and emission light filters in openings of the cover 290" correspond to positions of the pairs of emission light generators 220" and excitation light sensors 230" on the carrier 280". The carrier 280" and the cover 290" are rectangular with substantially matching outer dimensions.

FIG. 8 shows the calibration device 200" of FIG. 7 installed in the thermal cycler of FIG. 6. The arrangement of the calibration device 200" in the thermal cycler is shown schematically. In particular, the protection cover 290" and the carrier 280" are shown separately from each other in order to illustrate the course of emission light beams 165a,b. Each temperature sensor 210" of the calibration device 200" is inserted into a corresponding sample well 140 a,b in the reaction zone of the thermal cycler. Hence, the temperature may be sensed inside the sample wells 140. This allows for a precise measurement of the reaction conditions. Opposite each temperature sensor 210", a pair of excitation light sensors 230" and emission light generators 220" is provided on the carrier's top side. Using a switch (not shown) of the calibration device, that means by selecting one of the control circuitry modes, the user can select to dynamically measure the temperature when the switch is in a position (A), to measure temperature and to alter the emission light based on the sensed temperature when the switch is in another position (B), to measure the temperature to alter the emission light based on the average temperature when the switch is in another position (C), to measure temperature and to alter the emission light based on the sensed excitation light when the switch is in another position (D). The switch may, in particular, comprise in electrically and/or mechanically actuated switch like, for example a switch panel. In this embodiment, the user may conveniently choose whether to calibrate the thermo cycler for temperature, optics and optical detector, optics and excitation light distribution and/or any combination of temperature, optics and excitation light distribution. The user may switch the calibration device 200" to a mode (B) in which the emission light emitted by each emission light generator 220" is indicative of the temperature measured by the temperature sensor 210". The emission light beams 165a,b generated by the emission light generator 220" pass through respective emission light filters 225" provided in openings of the cover 290". From there, the beams 165*a,b* are guided to the optical detector 110 of the thermal cycler. As FIG. 8 only shows a schematic diagram, further elements of the thermal cycler like, for example, emission and excitation light filters, lenses and mirrors, are not shown. However, it is to be understood that for the thermal cycler of FIG. 8, the optical detector 110 may be movable and/or the thermal cycler may comprise one or more adjustable mirrors and/or lenses.

In FIG. 9, a schematic drawing of a known thermal cycler is shown. The thermal cycler comprises a reaction zone 340, in which a test tube 341 may be arranged. The thermal cycler further comprises a heater (not shown) that is configured to heat up the reaction zone 340 and, thereby, also the sample contained in the test tube 341. In particular, the thermal cycler may be configured to subject the sample contained in the test tube 341 to a temperature cycle using the heater. The thermal cycler further comprises an excitation light source 320 with excitation light optics 322 and an excitation light filter 321. In particular, the thermal cycler may comprise an excitation light filter wheel having a plurality of excitation light filters 321 corresponding to different wavelengths. By turning the excitation light filter wheel, an excitation light filter 321 corresponding to a desired wavelength may be put in the light path of the excitation light source 320. An excitation light beam 360 passes from the excitation light source 320 through the excitation light optics 322 and the excitation light filter 321 into the test tube 341. The sample contained in the test tube 341 includes a fluorescent label, such that emission of fluorescence light from the sample is indicative of an amount of a desired sequence. The emission light beam 365 emitted by the sample passes through an emission light filter 311 of the thermal cycler. Similar to the excitation light filter 321, the thermal cycler may comprise an emission light filter wheel having a plurality of emission light filters 311 with different wavelengths. Further, the thermal cycler comprises emission light optics 312. The emission light passes from the sample in the test tube 341 through the emission light filter 311 and the emission light optics 312 to the optical detector 310 of the thermal cycler. The intensity of the emission light detected by the optical detector 310 is indicative of an amount of a desired sequence in the sample contained in the test tube 341.

In FIG. 10A, a calibration device 200''' according to the invention is shown. The calibration device is positioned in the thermal cycler of FIG. 9. The calibration device of FIG. 10A has a carrier 480 with tube 341' configured for calibration purposes. In particular, the calibration device comprises a temperature sensor 410 and an excitation light sensor 430 with an excitation light filter arranged at a first end of the calibration device. The temperature sensor 410 and the excitation light sensor 430 are electrically coupled by a wire to the second end of the calibration device, from where an electric coupling 445 extends to control circuitry 240''' of the calibration device which is mounted on the carrier 480. With this arrangement, the temperature and the excitation light are sensed at a position deep within the receiving space, thus providing a high precision of measurement. The calibration device further comprises an emission light generator 420 and an emission light filter 425 arranged at the second end. The emission light generator 420 is also coupled to the control circuitry of the calibration device via coupling 445.

The control circuitry of calibration device 200''' has one or more selectable control circuitry modes. For example, the user may select to dynamically measure the temperature when the switch is in a position (A), to measure temperature and to alter the emission light based on the sensed temperature when the switch is in another position (B), to measure temperature and to alter the emission light based on the average sensed temperature when the switch is in another position (C), to measure the temperature and to alter the emission light based on the sensed excitation light when the switch is another position (D). Different modes may be activated by a switch which may, in particular, comprise an electrically and/or mechanically activated switch. If the user switches the calibration device 200''' to a mode (B) in which the control circuitry controls the intensity of the emission light generated by the emission light generator 420 based on the temperature sensed by temperature sensor 410 and/or based on the excitation light intensity sensed by excitation light sensor 430. The emission light generated by the emission light generator 420 passes through the emission light filter 425 towards the calibration device's first end. By scattering processes, the emission light 366 is provided towards the periphery of the calibration device. The emission light is scattered towards the optical detector 310 as indicated by arrows 365 and 366 in FIG. 10A. Hence, the temperature and the excitation light intensity may be monitored inside the sample well using the existing components of the thermal cycler of FIG. 9. The control circuitry 240" may be mounted on the carrier 480 by a micro-PCB connector, soldering, welding, clamping and/or gluing. The control circuitry 240" is equipped with an interface for wireless communication and a socket.

FIG. 10B shows a calibration device 200"" according to the invention. The calibration device 200"" comprises a circular carrier 480' which is equipped with the plurality of tubes 341' configured for calibration purposes. The calibration device 200"" comprises control circuitry 240" that is mounted in a central part of the carrier 480'.

Further modifications of the preferred embodiments are possible without leaving the scope of the invention which is defined by the claims. In particular, the calibration device may comprise more than 16 emission light generators. The number of emission light generators of the calibration device may be equal to a number of sample wells in the reaction zone of the thermal cycler. In some embodiments, the control circuitry adjusts the length of an emission light pulse generated by the emission light generator based on the ambient condition measured by one of the ambient condition sensor. In some embodiments, the thermal cycler of the invention may be configured to store an intensity of emission light detected by the optical detector for later use. As the detected intensity is indicative of a temperature level inside the sample well, this corresponds to storing a temperature of the reaction zone. Further, the thermal cycler may be configured to control the heater based on the stored emission light intensity. Hence, with the user entering a desired temperature or temperature range, the thermal cycler may adjust the heating, such that the desired temperature or temperature range is reached in the sample wells, using the stored intensity as a calibration parameter.

In some embodiments, the thermal cycler is configured to control a temperature of the reaction zone according to a series of temperature levels of 30° C., 95° C., 30° C., 90° C., 50° C., 70° C., 60° C. and 30° C., keeping the temperature substantially constant at each of these levels for at least about 3 min. In some embodiments, the thermal cycler is configured to control a temperature of the reaction zone according to a series of temperature levels of 30° C., 95° C., 30° C., 95° C., 50° C., 70° C. and 30° C., keeping the temperature substantially constant at each of these levels for at least about 1 min. When reaching the temperature of 70° C., the thermal cycler may be configured to provide excitation light and to detect emission light from within the reaction zone. Hence, the calibration takes place at that temperature level. Alternatively, the thermal cycler may be configured to heat the reaction zone to about 65° C. and from there to about 80° C., in particular, at a constant rate, e.g. of about 0.1° C./min. The emission light from within the reaction zone may be detected by the optical detector at regular time intervals, e.g. every 45 s.

The invention claimed is:

1. A calibration device for use in calibrating a thermal cycler having a reaction zone, an excitation light source and an optical detector, the calibration device comprising:
   one or more ambient condition sensors comprising at least one temperature sensor, each adapted to sense an ambient condition at a respective position within the reaction zone,
   one or more emission light generators, adapted to be in optical communication with the optical detector, which generates an emission light at different positions within the reaction zone; and
   control circuitry, coupled to the one or more ambient condition sensors and to the one or more emission light generators, which alters at least one of the spectrum, intensity, and duration of the generated emission light;
   wherein, during calibration of the thermal cycler, the control circuitry alters the emission light generated by the one or more emission light generators based on the ambient condition sensed by the at least one temperature sensor.

2. The device of claim 1, wherein the one or more ambient condition sensors further comprise one or more excitation light sensors.

3. The device of claim 1, wherein the control circuitry is further configured to control a mode of operation, wherein a mode of operation is at least one of:
   a mode A, wherein the control circuitry is configured to store one or more temperatures sensed by one or more temperature sensors,
   a mode B, wherein the control circuitry is configured to alter the emission light based on one or more temperatures currently sensed by one or more temperature sensors,
   a mode C, wherein the control circuitry is configured to alter the emission light based on an average of one or more temperatures sensed by one or more temperature sensors, and
   a mode D, wherein the control circuitry is configured to alter the emission light based on excitation light sensed by one or more excitation light sensors.

4. The device of claim 1, wherein the control circuitry is further configured to store the sensed ambient condition.

5. The device of claim 1, further comprising an interface for transmitting signals indicating the sensed ambient condition.

6. The device of claim 1, wherein the one or more ambient condition sensors and the one or more emission light generators are arranged in pairs.

7. The device of claim 1, further comprising a carrier with top and bottom sides, wherein the one or more emission light generators are located on the top side of the carrier.

8. The device of claim 7, wherein the one or more temperature sensors are arranged on the bottom side of the carrier.

9. The device of claim 1, wherein the one or more ambient condition sensors further comprise one or more excitation light sensors and wherein the device further comprises one or more excitation light filters positioned in the light path of the one or more excitation light sensors.

10. The device of claim 1, further comprising one or more emission light filters positioned in the path of the emission light generated by the one or more emission light generators, wherein each emission light generator is associated with a corresponding emission light filter.

11. A thermal cycler comprising a reaction zone, an excitation light source, an optical detector and the calibration device of claim 1.

12. A method for calibrating a thermal cycler, according to claim 11, comprising:
   sensing an ambient condition at one or more positions within the reaction zone, and generating one or more emission light beams, said emission light beams being indicative of at least one of the sensed ambient condition and an average ambient condition sensed at said one or more positions.

13. The method of claim 12, wherein the one or more emission light beams is generated in the vicinity of the one or more positions within the reaction zone.

14. A machine-readable medium containing instructions to be executed by the thermal cycler of claim 11, wherein the thermal cycler further comprises a heater adapted to heat the reaction zone, wherein the instructions when executed cause the thermal cycler to execute the following steps:
   detecting emission light generated in the reaction zone using the calibration device of the thermal cycler, the emission light being indicative of a temperature at a position within the reaction zone or being indicative of an average temperature at one or more positions in the reaction zone,
   storing a parameter of said detected emission light, and
   controlling the heater at least partially based on the stored parameter.

15. A machine-readable medium containing instructions to be executed by the thermal cycler of claim 11, wherein the instructions when executed cause the thermal cycler to execute the following steps:
   detecting emission light generated in the reaction zone using the calibration device of the thermal cycler, the emission light being indicative of incoming excitation light at a position within the reaction zone,
   storing a parameter of said detected emission light, and
   providing excitation light by the excitation light source at least partially based on the stored parameter.

16. The device of claim 3, wherein the control circuitry is configured to be switched to one or more of modes A through D.

17. The thermal cycler, according to claim 11, further comprising a heater.

18. The thermal cycler, according to claim 17, further comprising a memory coupled to the optical detector and adapted to store a parameter detected by the optical detector, such that the thermal cycler performs at least one of heating the reaction zone based on the stored parameter and providing excitation light from the excitation light source based on the stored parameter.

* * * * *